United States Patent [19]
Renner et al.

[11] Patent Number: 6,083,151
[45] Date of Patent: Jul. 4, 2000

[54] MEDICAL INSTRUMENT HAVING A TUBE-LIKE ELEMENT AND A BENT HANDLE IN COMBINATION WITH AN ENDOSCOPE AND CAMERA MODULE

[75] Inventors: Klaus Renner; Klaus M. Irion, both of Liptingen; Horst Dittrich, Immendingen; Jürgen Rudischhauser; Rudi Klumpp, both of Tuttlingen, all of Germany

[73] Assignee: Karl Storz GmbH & Co. KG, Germany

[21] Appl. No.: 09/211,596

[22] Filed: Dec. 14, 1998

Related U.S. Application Data

[63] Continuation of application No. PCT/EP98/02079, Apr. 9, 1998.

[30] Foreign Application Priority Data

Apr. 14, 1997 [DE] Germany .......................... 197 15 507

[51] Int. Cl.⁷ .................................................. A61B 1/267
[52] U.S. Cl. ........................ 600/114; 600/112; 600/131; 600/132; 600/188

[58] Field of Search ...................... 600/101, 112, 600/114, 122, 125, 131, 132, 136, 138, 188, 197, 160

[56] References Cited

U.S. PATENT DOCUMENTS

| | | | |
|---|---|---|---|
| 5,088,819 | 2/1992 | Store | 600/137 |
| 5,695,448 | 12/1997 | Kimura et al. | 600/121 |
| 5,954,632 | 9/1999 | Heckele et al. | 600/131 |

*Primary Examiner*—John P. Leubecker
*Attorney, Agent, or Firm*—St. Onge Steward Johnston & Reens LLC

[57] ABSTRACT

A medical instrument has a tube-like element, a handle bent off from said tube-like element, an endoscope having a shaft, a camera module connected to said endoscope, a light pipe and a guide provided on said tube-like element for receiving said shaft of said endoscope. The endoscope is provided with at least two coupling elements extending in a direction of said bent-off handle and into an inside of said handle, one of said at least two coupling elements is coupled to said light pipe, another of said at least two coupling elements is coupled to said camera module, and said camera module is disposed inside of said handle.

11 Claims, 5 Drawing Sheets

MEDICAL INSTRUMENT HAVING A TUBE-LIKE ELEMENT AND A BENT HANDLE IN COMBINATION WITH AN ENDOSCOPE AND CAMERA MODULE

This application is a continuation of pending international application PCT/EP98/02079 filed on Apr. 9, 1998, which designated the United States.

BACKGROUND OF THE INVENTION

The present invention relates to a medical instrument having a tube-like element and a handle bent off therefrom, further an endoscope connected with a camera module, a guide provided on the tube-like element for receiving a shaft of the endoscope, and a light pipe. The instrument finds its preferred application as mediastinoscope, laryngoscope or diverticuloscope.

A medical instrument of this kind has been known from applicant's catalogue "ENDOSKOPE UND INSTRUMENTE FÜR HNO" (Endoscopes and Instruments for E.N.T.), $_5$th edition, 1/1996, sheets LA2C, LA3D and LA2D.

A video laryngoscope after Kantor/Berci, model II, illustrated in that publication, comprises a laryngoscope as a first assembly. The laryngoscope comprises a tube-like element with a bent-off handle projecting therefrom.

The term tube-like element as used in the context of the present invention is meant to describe tubular, semi-tubular or spatula-shaped elements, possibly also tapering elements, that can be introduced into body cavities, for example a trachea, a thorax, or the like. The projecting handle is bent-off from the tube-like element at an angle of 90° or a little less, and serves to bring the tube-like element into the desired position. Operating instruments are introduced through the tube-like element, or laterally from the side.

In order to permit the site of the operation to be observed visually, the tube-like element is provided with a guide, which in the case of the before-mentioned video laryngoscope is arranged on the outside of the tube-like element, into which an elongated shaft of an endoscope is introduced. At the proximal end, the endoscope projects a long way beyond the tube-like element. An optical connection projecting from the proximal end of the endoscope, in most cases offset relative to the handle by an angle of 90° about the tube-like element, has attached to it either an eyepiece or a camera module of a video camera. The camera module is connected via corresponding lines to an image processing unit and to a monitor.

Another connection piece for a light pipe, projecting from the proximal end of the endoscope, extends substantially in the plane of the handle, but proximally behind the latter, substantially at a right angle laterally way from the endoscope shaft. The light pipe serves to supply light from a light source to the operation site. It is then possible to guide the light to the distal end either via a separate line provided on the tube-like element, or directly inside the endoscope shaft.

The complete assembly of the medical instrument now comprises, viewed from the distal toward the proximal end along the longitudinal axis of the tube-like element, at least three elements, namely firstly the bent-off handle, secondly the light pipe socket projecting therefrom in offset arrangement, together with the camera module attached thereto and the outgoing lines, and thirdly the light pipe socket that is to be connected to a light source via a light pipe.

The three different components, projecting in different directions, obstruct on the one hand the site of the operation and especially the operator who has to carry out the operation with the aid of the operating instruments proper through the tube-like element.

On the other hand, the laterally projecting elements tend to exert a torque on the tubular element, once it has been placed in the desired position, so that there is a risk that the tubular element may be rotated over time in the course of the operation or even abruptly in case a person should get into contact with the connection lines. One has tried to remedy these problems by additional measures, for example by securing the handle in its position by means of widely spread chest supports. Although this may possible prevent the element from turning, it once more requires the use of an additional bulky, rod-like structure which obstructs the operator still further.

Now, it is the object of the present invention to overcome this problem and to provide a medical instrument of the type described above, which can be handled with much more ease and which, especially, has a considerably smaller overall size.

SUMMARY OF THE INVENTION

This object is achieved according to the invention by the fact that the endoscope comprises at least two coupling elements extending in the direction of the bent-off handle and into its inside, for being coupled to a light pipe and for being coupled to the camera module, and that the camera module is enclosed inside the handle.

Providing the two bent-off coupling elements in such a way that they project into the handle and into its inner space has the effect that they no longer project beyond the tube-like element and no longer form bulky connections that can be seen from the outside or have a disturbing effect. Both connections, i.e. the connection for the light pipe and the camera module, i.e. the connection that transmits the image, now extend into the inner space of the handle so that they are protected by the handle from inadvertent contacts or impairment. As the camera module is now also accommodated in the handle, all those elements, which in the case of the prior art projected from the tube-like element like spikes, are now enclosed in the handle in a compact configuration. The only elements that still project from the end of the handle are the cables that connect the light pipe with the light source and the camera module with the image processing system. The operator now can perform the operation through the tube-like element without being hindered by the components and/or the connections of the endoscope and the camera. The outer site of the operation now is no longer obstructed by bulky connections.

In one embodiment of the invention, both the tube-like element and the handle are provided with one opening each at their proximal ends through which the endoscope and the camera module can be introduced.

This feature provides the advantage that the assembly of the different components of the medical instrument for carrying out the operation, and the disassembly after completion of the operation, for example for the purpose of sterilizing the different parts, can be carried out in a simple way by introducing and/or pulling off the endoscope and the camera module from the proximal end. This helps to further facilitate handling of the medical instrument before and after the operation.

In a further embodiment of the invention, the openings are configured in such a way that an endoscope and camera module assembly can be introduced from the proximal toward the distal end.

This feature provides the considerable advantage that the endoscope component and the camera module component can be assembled to one unit and checked for proper function already before being introduced into the medical instrument. The complete unit then only has to be introduced into the tube-like element and/or the handle from the proximal end.

In a further embodiment of the invention, the endoscope and the camera module can be introduced via the openings separately, and can be coupled inside the instrument.

This feature is of particular advantage if very long and extremely thin endoscope shafts are used. In that case it is, for example, possible to introduce at first the endoscope from the proximal end into the tube-like element, without the connections of the light pipe and without the camera module. Thereafter, the camera module with its connection lines is introduced via the handle and coupled inside the latter with the endoscope already in place.

In a further embodiment of the invention, the endoscope can be detachably locked on the instrument, and the camera module can be detachably connected with the coupling elements of the endoscope.

This feature provides the advantage that the two options described above, i.e. inserting at first the endoscope alone, or inserting the assembled unit, lead to one and the same locked condition between the inserted components and the tube-like element or the handle, because locking is effected on the endoscope.

The fact that the camera module can be detachably connected with the coupling element of the endoscope allows again both mounting methods to be carried out easily and in a favorable way. Specifically, the two components, namely the endoscope and the camera module, can be coupled one with the other outside the medical instrument as such, and can then be fitted as an assembled unit, or else the endoscope can be inserted first, whereafter the camera module can be inserted and coupled with the endoscope already in place.

In a further embodiment of the invention, the inner contour of the handle and the outer contour of the camera module are mutually adapted in such a way that the camera module, coupled with the endoscope, can be pulled off only in the longitudinal direction of the handle.

This feature is of particular advantage if endoscopes with extremely thin and long shafts are to be inserted. When the endoscope and camera module assembly are pulled off the handle proximally, and if the endoscope shaft is very long and thin, then the entire unit must first be completely pulled off the tube-like element and must be exactly guided during this process along the longitudinal axis of the thin endoscope shaft. However, since the unit must of course be gripped somehow, this is advantageously effected by means of the cables that project from the lower or outer end of the handle. This point being, however, remote from the thin endoscope shaft by the length of the handle, there is a risk that not only a linear pulling-off movement but also a certain pivotal movement may occur during the pulling-off action with the resulting risk that the endoscope shaft may break or get detached from the remaining endoscope housing. The feature proposed by the present invention forces the user to uncouple and pull off at first the camera module in the longitudinal direction of the handle, before the endoscope can be pulled off the tube-like element. In this case, the endoscope can then be gripped at the rear end of the tube-like element, and can be pulled off without the other components, such as the light pipe and the camera module, which in some cases can be relatively heavy, being still attached to it. This also considerably improves the ease of handling.

In a further embodiment of the invention, the camera module comprises a movable bolt element that can be operated from the outside through the opening of the handle.

This feature provides the advantage that the endoscope and the camera module, received in the handle, can be detached from the outside by actuating the bolt without this operation requiring the use of special attention or special tools.

In a further embodiment of the invention, the camera module is provided with a focusing device comprising a set-collar that can be actuated from the outside through the opening of the handle. This feature likewise provides the handling advantage that the endoscope/camera module assembly can be focused to obtain a sharp picture after fitting of the endoscope/camera module assembly.

In a further embodiment of the invention, the handle exhibits a substantially U-shaped cross-sectional profile, with the opening of the U representing the proximal opening of the handle.

This feature offers the advantage to provide a handle that can be easily produced and can be grasped ergonomically and that comprises the desired openings which permit the camera module or, if necessary, the endoscope and camera module assembly to be introduced into the handle and/or the tube-like element.

In a further embodiment of the invention, the handle is provided with another opening at its outer end.

This feature provides the advantage that both assembly variants are rendered possible with such a handle, i.e. inserting the camera module from the proximal end or from the outer end of the handle, along its longitudinal axis.

In a further embodiment of the invention, the handle is provided with a sterile cover.

This feature provides the advantage that once the camera module, which in itself is not a sterile unit, has been introduced the sterile cover is applied whereby the medical instrument is protected in a sterile way in the areas where non-sterile components have been fitted before.

It is understood that the features mentioned above and those yet to be explained below can be used not only in the respective combinations indicated, but also in other combinations or in isolation, without leaving the context of the present invention.

BRIEF DESCRIPTION OF THE DRAWING

The invention will be described in more detail and explained below with reference to certain selected exemplifying embodiments and the attached drawings. In the drawings.

DETAILED DESCRIPTION OF PREFERRED EMBODIMENTS

Figure 1:
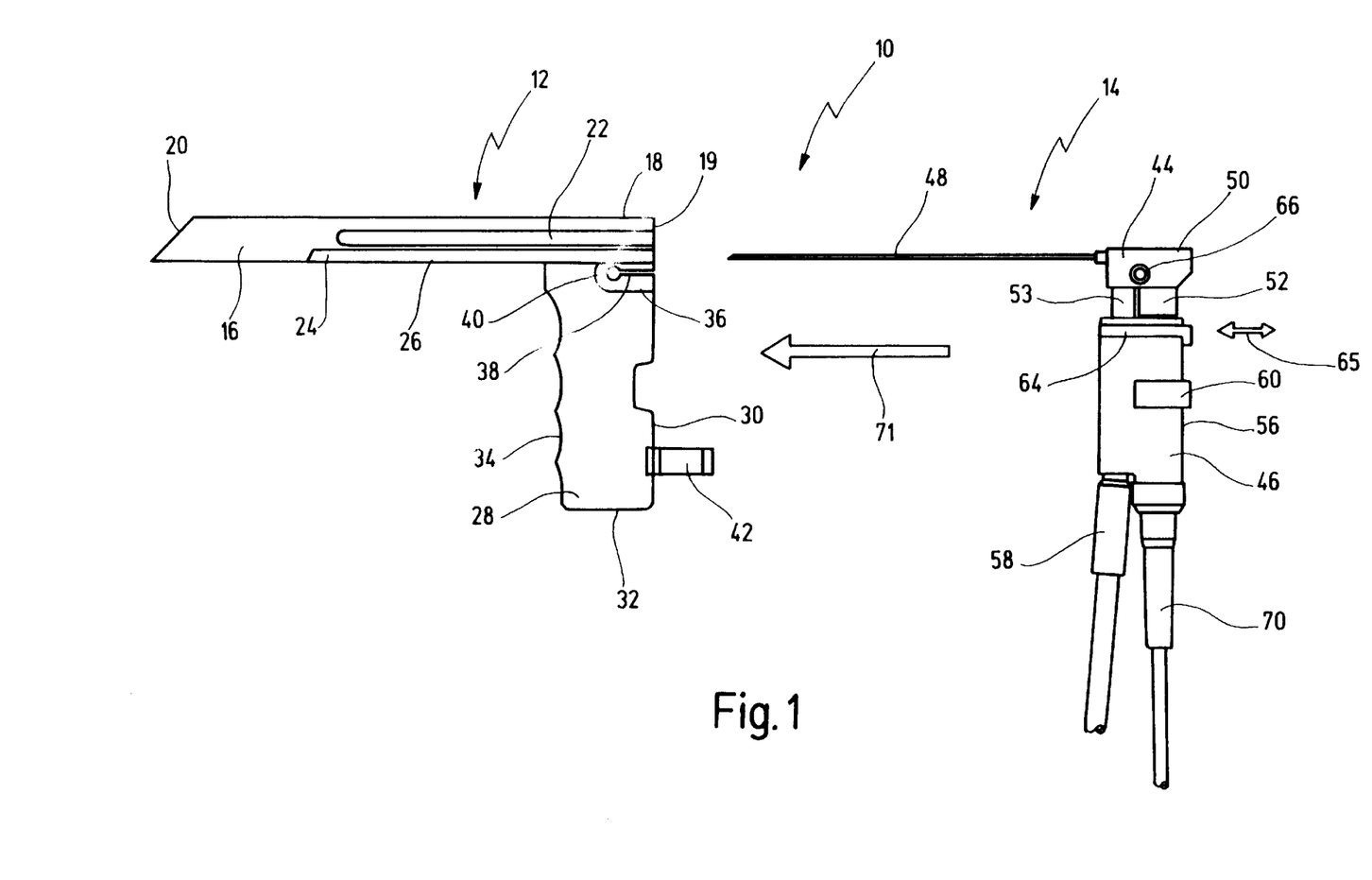
FIG. 1 shows a side view of a first embodiment of a medical instrument before a first assembly, comprising the tube-like element and the handle, is assembled with a second assembly, comprising the endoscope and the camera module.
Figure 2:
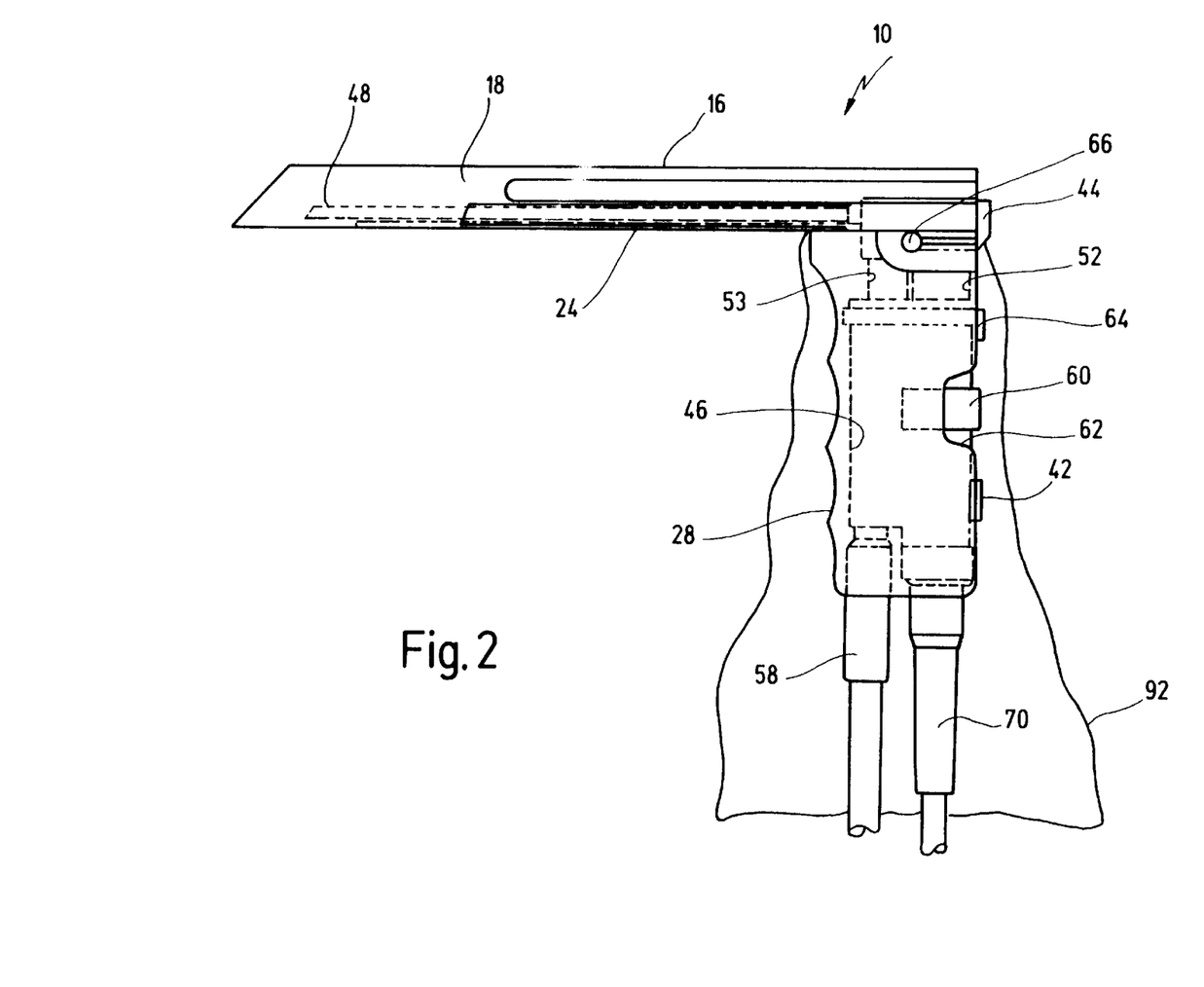
FIG. 2 shows the two assemblies, which are still unassembled in FIG. 1, in the assembled condition, with a sterile cover additionally applied on the handle.
Figure 3:
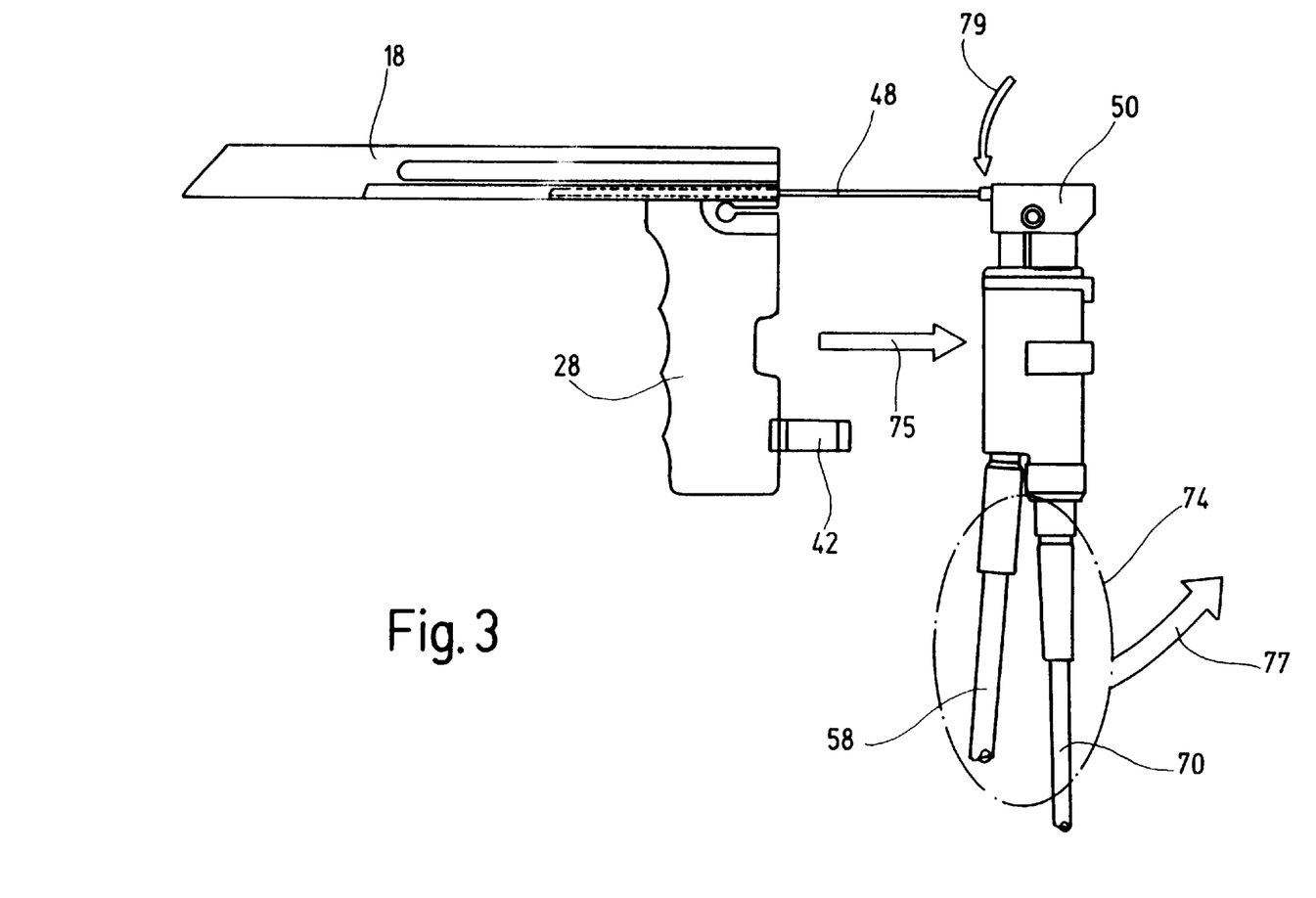
FIG. 3 shows a situation during disassembly of the medical instrument according to FIG. 2.

FIGS. 1 to 3 show a first embodiment of a medical instrument, indicated generally by reference numeral 10.

As can be seen best in FIG. 1, the medical instrument 10 comprises a first assembly 12 and a second assembly 14.

The first assembly 12 is a mediastinoscope and comprises a tube-like element 16 in the form of a cylindrical tube 18. The tube 18 is open, i.e. exhibits an opening 19, at its proximal end while the opposite distal open end is beveled, i.e. provided with a pointed end 20.

The tube 18 is provided with a lengthwise extending open slot 22 so that instruments can be introduced into the tube 18 not only from the proximal end, via the opening 19, but also laterally. Inside the tube 18, there is provided a guide 24 in the form of a thin tube 26, the purpose and intent of which will be described further below. The thin tube 26 is fixed to the inside of the tube 18 by soldering.

A handle 28 provided on the proximal end of the tube 18 projects from the latter substantially at a right angle.

As will be described further below with reference to FIG. 5, the handle 28 exhibits a substantially U-shaped cross-sectional profile whose distal area is provided with a finger depression 34 for receiving the fingers of a human hand.

The handle 28 is open, i.e. provided with a passage opening 30, at its proximal end and is likewise open, i.e. provided with an opening 32, at its lower outer end.

At the upper end in the representation of FIG. 1, i.e. in the area where the handle 28 is connected with the tube 18, a depression 36 is provided along which a proximally open longitudinal slot 38 extends in parallel to the longitudinal center axis of the tube 18, the slot 38 terminating at its closed end by an enlarged area 40.

A bolt flap 42 is provided to close the opening 32, at least in part.

The second component 14 comprises an endoscope 44 and a camera module 46.

The endoscope 44 comprises a long, thin cylindrical shaft 48, whose length corresponds substantially to the length of the tube 18 of the tube-like element 16 and which can be introduced into the guide 24 inside the tube 18. This means that the outer diameter of the shaft 48 corresponds substantially to the clear inner diameter of the thin tube 26.

At the proximal end, the shaft 48 is connected with a housing 50 from which two coupling elements 52 and 53, the detailed design of which will be described further below with reference to FIGS. 4 and 5, project at an angle of approximately 90° relative to the shaft axis.

The coupling elements 52 and 53 connect the endoscope detachably with the camera module 46.

The coupling element 52 serves for coupling the image produced by the endoscope 44 into the corresponding imaging system of the camera module 46.

The coupling element 53 serves for coupling the light pipes of the endoscope 44, received in the shaft 48, with an outer light source.

The camera module 46 comprises a housing 56 provided, on its end facing the coupling elements 52 and 53, with corresponding female recesses that can be positively engaged by coupling elements 52 and 53.

A light pipe 58 projecting from the opposite end of the housing 56 is connected with a light source not indicated in detail in the drawing, and guides the light from the light source to the coupling element 53.

A line 70 connected to the same end supplies the electric signal produced by the camera module 46 to an image processing unit.

That electric signal is produced by a CCD sensor (charge-coupled-device sensor), not indicated in detail in the drawing, which is arranged in the camera module 46 and which converts the image produced by the endoscope to an electric signal which is then supplied to the outside via line 70.

In the camera module 46, there is further provided an optical lens arrangement as focusing means. A set-collar 60 serves to adjust the focusing means.

The end of the housing 56 of the camera module 46, that faces the coupling elements 52 and 53 of the endoscope 44, carries a bolt element 64, arranged for crosswise displacement, which can be moved toward and backward as indicated by double arrow 65.

The displaceable bolt element 64 enables the camera module 46 to be detachably connected with, or detached from, the endoscope 44 or its coupling elements 52 and 53.

Transversely to the longitudinal axis of the shaft 48, there project from the housing 50 of the endoscope 44 diametrically opposite locking pins 66 the exact design and function of which will be described further below with reference to FIGS. 4 and 5.

During assembly of the medical instrument 10 from the two components 12 and 14, one therefore initially couples the endoscope 44 and the camera module 46 one with the other.

Thereafter, the assembly so obtained is introduced into the first assembly 12 from the proximal to the distal end, as indicated by arrow 71 in FIG. 1. During this operation, the shaft 48 of the endoscope 44 is slid into the guide 24.

This sliding operating is continued until the locking pins 66 enter the longitudinal slot 38 on the handle 28—for which purpose they are urged to the inside—and until they reach the enlarged area 40. Once this area is reached, the depressed locking pins 66 can be released again so as to project and protect the second assembly 14 from being pulled off the first assembly 12. As a further security measure, the bolt flap 42 is now closed, whereby the assembly as illustrated in FIG. 2 is obtained.

The set-collar 60 of the camera module 46 is accessible from the outside, from the proximal end. In order to facilitate the adjustment of the set-collar 60, an additional recess 61 is provided in the handle 28 in this area.

The assembly is then provided with a sterile cover 92 in the form of a film.

FIG. 3 illustrates a particular situation during disassembly of the assembly. The sterile cover 92 has been removed, and the bolt flap 42 has been opened. Given the fact that the second assembly 14 is received inside the tube-like element 16 or inside the handle 28, it is gripped, for being pulled off, in the area of the lines 58 and 70 that project beyond the handle 28; this area is defined in the drawing by a dash-dotted line 74. For pulling off the second assembly 14, the later is pulled in the direction indicated by arrow 75 in FIG. 3.

If the second assembly 14 is gripped in the area 74, and if the shaft 48 of the endoscope 44 consists of an extremely long and thin tube with a diameter in the area of one millimeter, there is a risk that the operator may, thoughtlessly, perform a pivotal movement in conjunction with the pulling-off movement, as indicated by an arrow 77 in FIG. 3. This creates a heavy strain on the connection point between the shaft 48 and the housing 50 of the endoscope 44—this point being indicated in FIG. 3 by the point of arrow 79—so that any inattentiveness may result in a risk of the shaft 48 breaking off.

Figure 4:
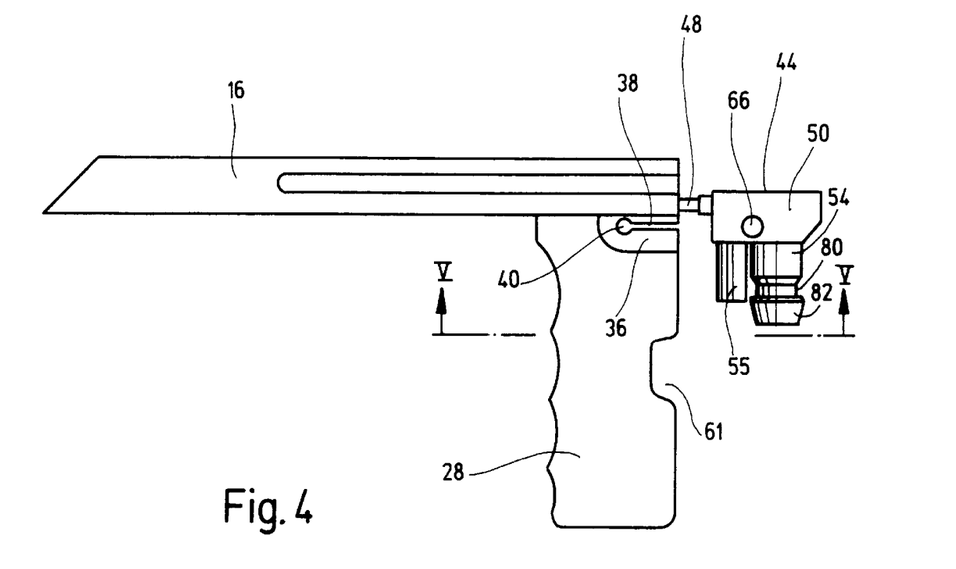
FIG. 4 shows another embodiment of a medical instrument during the first assembly step, where an endoscope is inserted into the tube-like element, but without the camera module.
Figure 5:
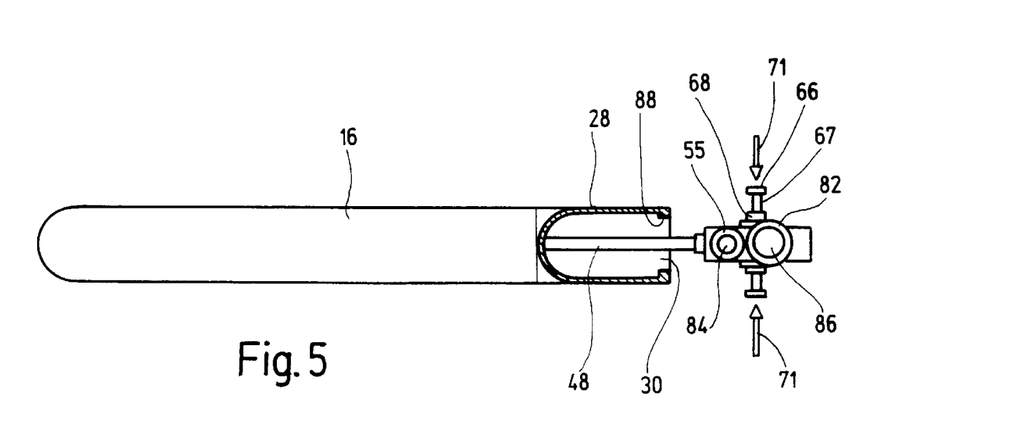
FIG. 5 shows a sectional view taken along line V—V in FIG. 4.
Figure 6:
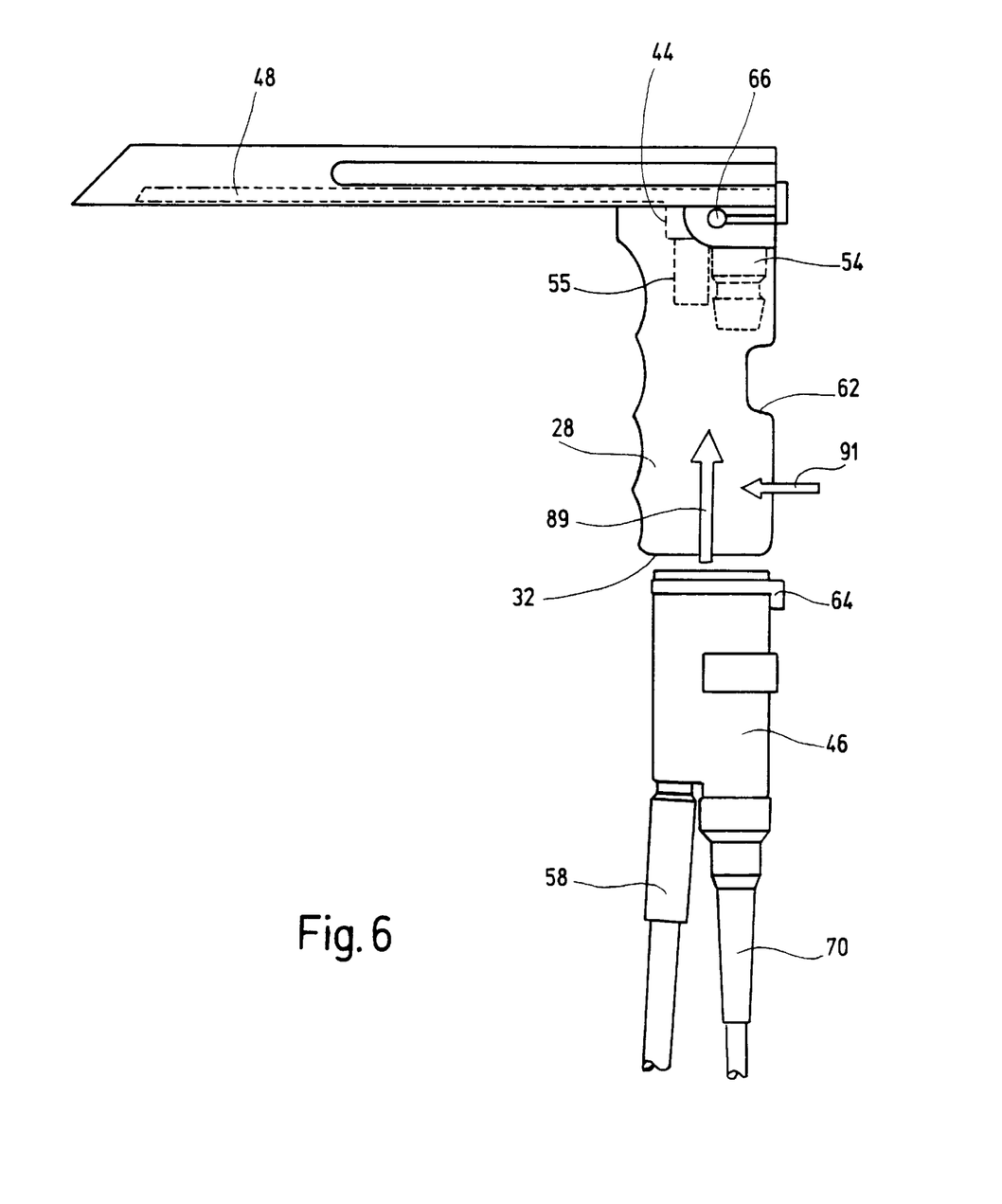
FIG. 6 shows a representation, comparable to that of FIG. 4, of another assembly phase where the camera module is inserted into the handle.

In order to exclude that risk with endoscopes having extremely thin shafts, the structure and/or assembly method illustrated in FIGS. 4 to 6 have been provided.

As can be seen in FIGS. 4 and 5, only the endoscope 44 is introduced or pulled off during assembly or disassembly. FIGS. 4 and 5 illustrate a situation where the thin shaft 48 has been introduced almost over its full length into the guide—not shown in detail in the drawing—of the tube-like element 16.

As can be seen in FIG. 5, the locking pins 66, that project radially from the housing 50 of the endoscope 44, are relatively long and comprise in addition to an end portion of disk-like shape a relatively thin section 67 and an inner, relatively thick section 68. The clear outer diameter of the thin section 67 corresponds substantially to the width of the longitudinal slot 48, the outer diameter of the thicker section 68 corresponds to the diameter of the enlarged area 40.

In the position illustrated in FIGS. 4 and 5, the spring-loaded locking pins 66 are not urged toward the housing 50, as indicated by arrows 71.

The thin sections 67 now occupy a position in which the locking pins 66 can be pushed through the longitudinal slot 38.

Once the closed end of the enlarged area 40 has been reached, the locking pins 66 are released, and are urged to the outside by the spring, not shown in detail, so that their inner, thicker section 68 comes to engage the enlarged area 40 of the longitudinal slot 38.

In order to ensure that the laterally projecting locking pins 66 will not interfere later with the operation, the recess 36 is provided in that area of the handle 28.

However, the recess makes it possible during disassembly to simply grip the locking pins 66 and push them to the inside, whereafter the endoscope 44 can be pulled off.

From the representation of FIG. 4 it is apparent that the coupling element 52 is designed as a cylindrical pipe socket 55, closed by a window 84, as can be seen in FIG. 5.

The pipe socket 55 serves as coupling means for the light pipe 58.

The further coupling element 52, extending in parallel at a certain distance, is likewise designed as pipe socket 54 and provided with an annular groove 80 followed by a cone 82.

As can be seen in FIG. 5, the cone 82 is likewise closed by a window 86.

The pipe socket 54 serves for supplying the image produced by the endoscope 44 to the outside.

To this end, the image that has been produced via a lens system inside the shaft 48, is fed by corresponding optical elements, such as prisms, laterally into the pipe socket where it is adapted, if necessary, to a size corresponding to the window 86 by means of an intermediate imaging system.

From the cross-sectional representation of FIG. 5 it is apparent that the handle 28 is provided with a narrow portion 88 on its proximal end in the area of its opening 30. This narrow portion 88 exists, however, only in the area between the recess 61 and tube-like element 16.

Consequently, the camera module 46 can be introduced into the handle 28 either in the manner illustrated in FIG. 6, through the opening 32, or laterally in the area between the recess 61 and the outer lower end of the handle 28, as indicated by arrows 89 and 91.

Thereafter, the camera module 46 is displaced along the arrow 89 until it gets into contact with the pipe sockets 54, 55.

The cone 82 of the pipe socket 54 then enters a corresponding opening, pushes the spring-loaded bolt element 64 to the side until it snaps into the annular groove 80. In this condition, the endoscope 44 is locked with the camera module 46, as shown in the illustration of FIG. 2.

The narrower portions 88 in the area of the handle between the recess 61 and the tube-like element 16 prevent that assembly from being pulled off in proximal direction.

For pulling it off, it is at first necessary to depress the bolt element 64 so that the latter disengages from the annular groove 80, whereafter the camera module 46 can be pulled off the pipe sockets 54 and 55, in a direction opposite to arrow 89, and can then be removed from the handle 28 either in the same direction or laterally in opposite direction to arrow 91.

Thereafter, the endoscope 44 can be removed by depressing the locking pins 66 and pulling off the endoscope. This operation can be carried out without any risk that a torque may be produced, as described in connection with FIG. 3, so that there does not exist a risk, in the case of thin endoscope shafts, that the shaft may break or be torn off.

We claim:

1. A medical instrument having a tube-like element, an endoscope having a shaft, a camera module connected to said endoscope, a light pipe, and a guide provided on said tube-like element for receiving said shaft of said endoscope, wherein said endoscope is provided with at least two coupling elements extending in a direction of said bent off handle and into an inside of said handle, one of said at least two coupling elements is coupled to said light pipe, another of said at least two coupling elements is coupled to said camera module, and wherein said camera module is disposed inside of said handle.

2. The medical instrument of claim 1, wherein said tube-like element and said handle are provided with an opening each at its proximal ends through which opening said endoscope and said camera module can be introduced.

3. The medical instrument of claim 2, wherein said openings are configured in such a way that an assembly consisting of said endoscope and said camera module can be introduced from a proximal towards a distal end of the medical instrument.

4. The medical instrument of claim 3, wherein said endoscope and said camera module can be introduced via said openings separately, and can be coupled inside the instrument.

5. The medical instrument of claim 1, wherein said endoscope can be detachably locked on said instrument, and said camera module can be detachably connected to said coupling elements of said endoscope.

6. The medical instrument of claim 1, wherein an inner contour of said handle and an outer contour of said camera module are mutually adapted in such a way that said camera module, coupled with said endoscope, can be pulled off only in a longitudinal direction of said handle.

7. The medical instrument of claim 1, wherein said camera module comprises a movable bolt element that can be operated from an outside through an opening of said handle.

8. The medical instrument of claim 1, wherein said camera module is provided with a focusing device comprising a set-collar that can be actuated from an outside through an opening of said handle.

9. The medical instrument of claim 1, wherein said handle exhibits a substantially U-shaped cross-sectional profile, said U-shaped profile opens proximal and provides a proximal opening of said handle.

10. The medical instrument of claim 1, wherein said handle is provided with an opening at its proximal end and is provided with another opening at its outer terminal end.

11. The medical instrument of claim 1, wherein said handle is provided with a sterile cover.

* * * * *